United States Patent [19]
Chikami et al.

[11] Patent Number: 5,271,733
[45] Date of Patent: Dec. 21, 1993

[54] DEVICE FOR CORRECTING TEETH IRREGULARITIES

[75] Inventors: Kunio Chikami, 211-1, Minamikuma, Kochi-shi, Kochi-ken; Hiroshi Komori, Saitama, both of Japan

[73] Assignee: Kunio Chikami, Kochi, Japan

[21] Appl. No.: 886,564

[22] Filed: May 21, 1992

Related U.S. Application Data

[63] Continuation-in-part of Ser. No. 678,422, Apr. 1, 1991, abandoned.

[30] Foreign Application Priority Data

| Apr. 3, 1990 | [JP] | Japan | 2-89661 |
| Mar. 26, 1992 | [JP] | Japan | 4-68482 |
| Mar. 26, 1992 | [JP] | Japan | 4-68483 |

[51] Int. Cl.$^5$ ............................. A61C 3/00
[52] U.S. Cl. ............................. 433/20; 433/8; 433/10
[58] Field of Search ............. 433/8, 9, 10, 20, 22

[56] References Cited

U.S. PATENT DOCUMENTS

| 2,495,692 | 1/1950 | Brusse | 433/20 |
| 2,821,020 | 1/1958 | Brusse | 433/20 |
| 3,043,007 | 7/1962 | Wallshein | 433/8 |
| 3,895,445 | 7/1975 | Silverman et al. | 433/9 |
| 4,172,323 | 10/1979 | Orlowski | 433/9 |
| 4,659,310 | 4/1987 | Kottemann | 433/20 |
| 4,850,865 | 7/1989 | Napolitano | 433/8 |
| 4,946,387 | 8/1990 | Adell | 433/20 |
| 5,015,180 | 5/1991 | Randklev | 433/9 |
| 5,092,941 | 3/1992 | Miura | 433/20 |
| 5,112,880 | 5/1992 | Tsunekawa et al. | 522/81 |

OTHER PUBLICATIONS

American Orthodontic Catalog VII, 1980, p. 103.

*Primary Examiner*—John J. Wilson
*Assistant Examiner*—Cindy A. Cherichetti
*Attorney, Agent, or Firm*—Armstrong, Westerman, Hattori, McLeland & Naughton

[57] ABSTRACT

A supplementary device for use in a device for correcting teeth irregularities includes a bracket having a slit with a T-shaped section and a wire to be inserted into the slit and engaged with the bracket. The wire has an elongated projection, and the supplementary device includes a wire engaging slit having substantially the same shape as the slit in the bracket. At least one protrusion is adapted for engaging a resilient band, and the bracket is slidable along the wire.

5 Claims, 15 Drawing Sheets

FIG. 7(a)
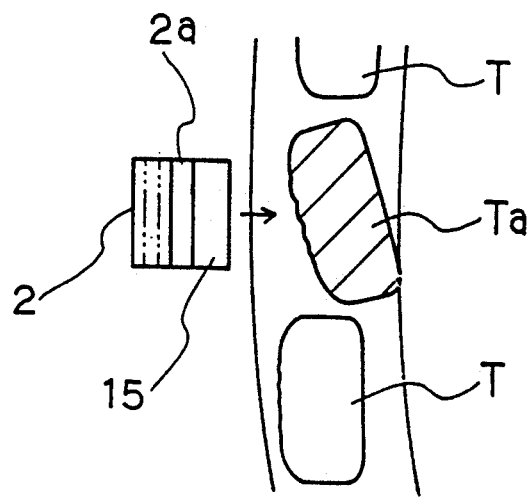
FIG. 7(b)
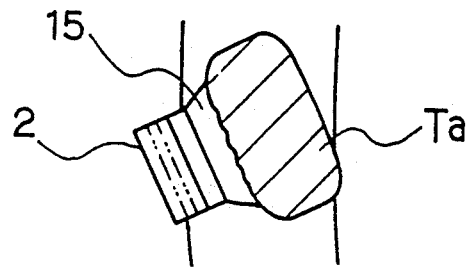
FIG. 7(c)
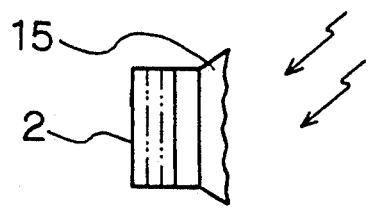
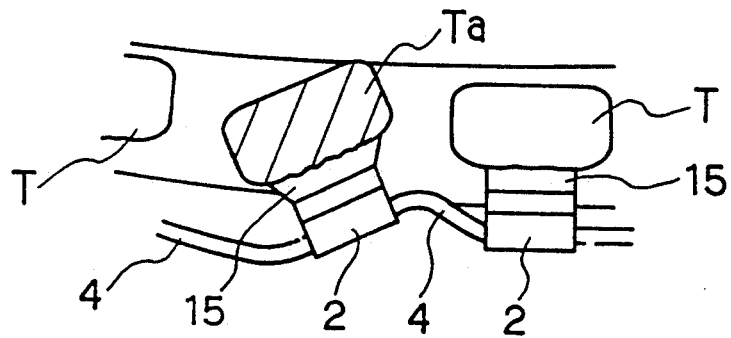
FIG. 7(d)

DEVICE FOR CORRECTING TEETH IRREGULARITIES

CROSS-REFERENCE TO RELATED APPLICATIONS

This is a continuation-in-part of application Ser. No. 678,422 filed on Apr. 1, 1991 and now abandoned.

BACKGROUND OF THE INVENTION

The present invention relates to a device for correcting teeth irregularities (malalignment), and more particularly, to a correcting device which can correct malalignment with no need of tying a wire to brackets.

A conventional correcting device has, for example, as shown in FIG. 21, brackets 52, a wire 53 and strings 54 for tying the brackets to the wire. Each bracket is provided with a slit (wire-engaging-slit) 51 for catching the wire 53. The wire 53 is inserted through a series of the slits of the brackets 52, and is supported thereby.

The wire 53 has a generally round shape in cross section, and sometimes a square shape.

In use of the device, each bracket 52 is fixed on each tooth T of the malalignment. The wire 53 is inserted through the series of slits 51 of brackets 52, and then, the wire 53 is bent in such way that spring force of the wire 53 is applied upon the teeth to correct the alignment, and the wire is tied on the brackets by means of the strings 54 with utilizing grooves 55 in the side surfaces of the brackets 52.

In the conventional device, it is very complicated to fasten the wire 53 to each bracket 52 and high skill is required, and moreover it takes much time to perform the fastening work. Especially, during the correction of malalignment, which may take a few months, the wire has to be changed to a new wire having higher elastic force several times, since the elastic force becomes weakened by gradual moving of the teeth.

Consequently, both the orthodontist and the patient complicated and laborious procedure whenever the wire is changed.

Further, in case a correcting torque is applied against the bracket by utilizing a square sectional wire in order to correct an inclination or twist of teeth, it is difficult to fasten the wire to the bracket, and highly refined technique is required for fixing the wire such that torque is sufficiently transmitted.

In addition, since the conventional wire is made of a metal, the wire is bright and conspicuous, and the appearance is bad in use. Further, users may have an adverse feeling about the wire.

In the conventional device, special brackets having cylindrical shape are used in order to fix both ends of the wire, and consequently, the patient feels disconfort in the mouth.

A main object of the present invention is to delete the above-mentioned problems and to provide a device for correcting teeth irregularities, which is easily attached to the teeth facilitates changing a wire, and creates a less adverse feeling in use.

Another object of the present invention is to provide a device for correcting teeth irregularities by using a plastic wire which has high resistance to creep and has large geometrical moment of inertia of its cross sectional area.

In the conventional correcting method, it is difficult to fix the bracket to the tooth, wherein a twisted angle, inclined degree and the like are large and each shape is different, in the appropriate location and a angle.

Many kind of the bracket having different shapes of the surface to be contacted with the tooth have been conventionally prepared or processed in accordance with the shape of the tooth.

The object of the present invention is to provide a device for correcting teeth irregularities wherein the device corresponds to a tooth one-to-one and can be easily installed by providing the bracket with the base plate which can be easily processed so as to have a shape corresponding to each tooth.

As the tooth to be corrected, there are such case where the tooth is twisted, inclined, oblique, or a clearance between teeth is large. When the clearance between teeth is large, a sliding operation is required. When the twisted tooth is corrected, it sometimes happens that the sliding operation is required in the correcting step.

When one tooth is corrected by the sliding operation, the brackets which are fixed to the other teeth are corded up by a resilient material such as a rubber band to create the force of the sliding operation.

However, since the bracket is small (width is in the range from 1 to 5 mm, length is in the range of 1 to 5 mm), the rubber band is difficult to engage and sometimes slips off.

The present invention provides a supplementary device wherein an installation and removal can be easily performed.

SUMMARY OF THE INVENTION

In accordance with the present invention, there is provided a device for correcting teeth irregularites, comprising a bracket to be fixed on a tooth, said bracket having a slit with a T-shaped cross section, and a wire to be inserted into said slit and thereby be engaged with said bracket, said wire being provided with an elongated projection and having a "T" like shape in section.

BRIEF DESCRIPTION OF THE DRAWINGS

FIG. 7 is a schematic plan view illustrating an example of a method for installating the correcting device of FIG. 1;

DETAILED DESCRIPTION

Figure 1:
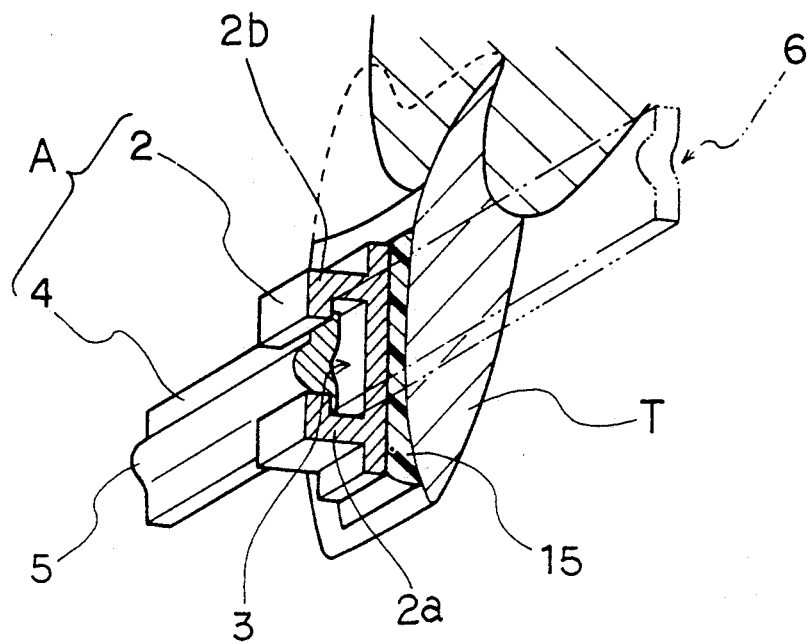
FIG. 1 is a perspective view partly in section, showing a main part of an embodiment of the correcting device of the present invention.
Figure 2:
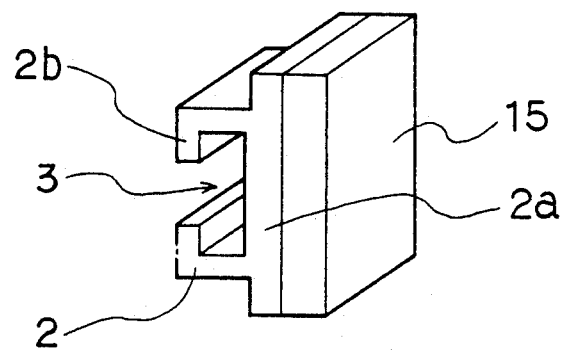
FIG. 2 is a schematic perspective view wherein a bracket in FIG. 1 is seen from the side of a base plate.

Referring to FIGS. 1 and 2, construction of a correcting device of the present invention is explained hereinafter.

FIGS. 1 and 2 show a main part of a correcting device A which is an embodiment of the present invention. The numeral 2 shows brackets attached to teeth T, and the numeral 4 shows a wire inserted through slits (wire-engaging-slits) 3 of the brackets 2. In the embodiment of FIG. 1, the correcting device A comprises the brackets 2 and the wire 4.

The bracket 2 has a flat base part 2a which is to be attached to the tooth T, and a pair of L-shaped nails 2b arranged on both the upper and the lower ends of the base part 2a respectively, so that they are facing each other. As a result, the pair of nail parts 2b build up a T-shaped slit 3 therebetween.

The bracket 2 can be made of dental alloy, ceramics, plastics or the like.

As the plastics material, dental resin such as polymethyl methacrylate, polyoxymethylene, polycarbonate, and the like, which has high strength, less moisture absorption and anti-plastic-deformation even in a moist atmosphere at 80° C. are preferably used.

However, another synthetic resin such as polyolefin, polyvinyl chloride, polyester and the like can also be used. Further, various fibrous or powdery fillers of ceramics, metal, glass and the like can be blended in the above-mentioned polymeric materials.

Metalic brackets are preferably to be coated with ceramics or plastics so as to become a neutral color (i.e. white, cream, or the like).

The above-mentioned wire 4 can be made of the same material as the bracket. However, materials having high resistance to creepage (advancing deformation due to stress), low sliding frictional coefficient and high durability against various germs or dirt in mouth are more preferable.

For example, a plastic tape molded together with (a) plastic filaments such as various kinds of polyester filaments, (b) the above-mentioned plastic filaments which are reinforced by blending inorganic crystal powder, organic powder, or inorganic or organic fine fibers, (c) glass fibers for core member, or the like can be preferably used.

Through various experiments, it is demonstrated that creep resistance (anti-creep strength) of bending stress of a plastic extruded wire often lessens due to extension of the wire.

Therefore, for instance, there is such a case that it is preferable that a plastic wire which is made by only extruding without extension, or which is obtained by extruding a plastic material, heating the extruded wire to the recrystallizing temperature thereof, and by cooling and curing. The mechanism of improving resistance to creep due to the heat treatment is not clear. However, it is considered that the directions of molecules of the plastics which has been oriented by extrusion become random when they are crystallized (unoriented crystallizing: a state that fine crystals are arranged in disorder) by the heat treatment. For example, as to polyester, preferable condition of thermal curing is approximately 30 sec to 2 minutes at 160° C.

Figure 3:
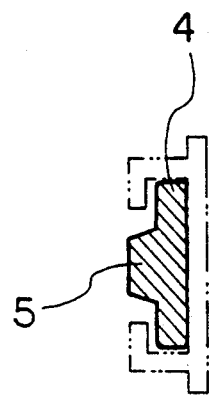
FIG. 3 is a sectional view illustrating a wire of the present invention.
Figure 4:
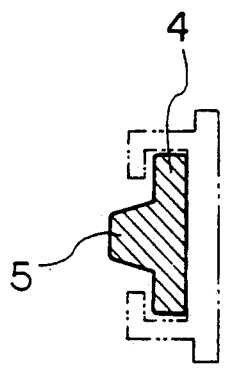
FIG. 4 is a sectional view illustrating another embodiment of the present invention.

As shown in FIGS. 3 to 4, a shape of the wire 4, wherein wire has an elongated projection on one side of surface thereof and has a "T" like shape in section, is employed. A geometrical moment of the inertia of such the wire having the elongated projections and having "T" like shape in section 2 to 8 times as large as the wire which has a rectangular shape in section. With respect to the above wire, which has the projection, the tooth of the malalignment can be corrected in multiple directions (three-dimensionally).

According to the present invention, the wire which has the projection has the shape in section as follows. A height of the protrusion ranges preferably from 0.1 to 1 when a widthwise length of the wire is 1. When the wire has the rectangular shape (width is 1.5 mm, thickness is 0.3 mm), the geometrical moment of the inertia of the wire is 0.0034 mm$^4$. On the contrary, when the wire is provided with the elongated projection (height of the projection is 0.3 mm, width is 0.4 mm), the geometrical moment of the inertia of the wire is 0.0128 mm$^4$. When the wire is provided with the elongated projection (height of the projection is 0.6 mm, width is 0.4 mm), the geometrical moment of the inertia of the wire is 0.0423 mm$^4$. Further, with respect to the wire having an elongated groove as shown in FIG. 5, the wire is preferably provided with the groove, wherein width ranges from 0.1 to 0.5 mm and depth ranges from 0.005 to 0.3 mm, substantially in the center of the other side of the surface of the wire.

Figure 5:
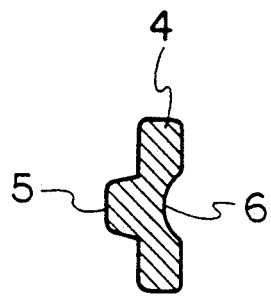
FIG. 5 is a sectional view illustrating yet another embodiment of the present invention.
Figure 19:
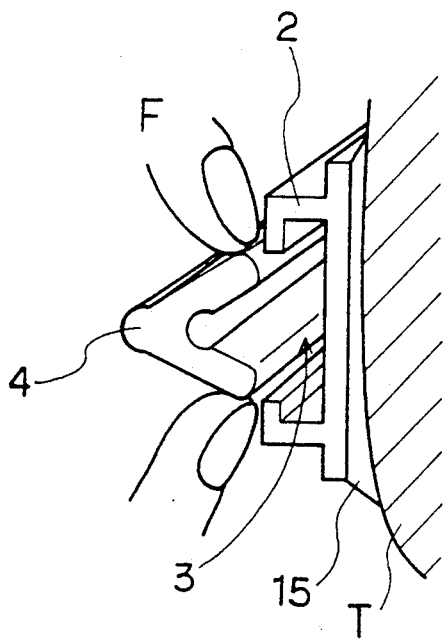
FIG. 19 is a perspective view partly in section, showing a main part of an example showing a method for installating the wire of the present invention.

Further, as shown in FIG. 5, when a wire 4 having a groove 6 extending along a longitudinal direction of the wire is used, the wire can be easily and straightly folded as shown in FIGS. 19 by means of fingers F or the like.

Figure 6:
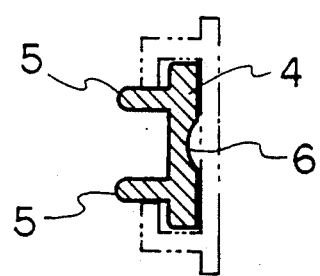
FIG. 6 is a sectional view illustrating yet another embodiment of the present invention.
Figure 8:
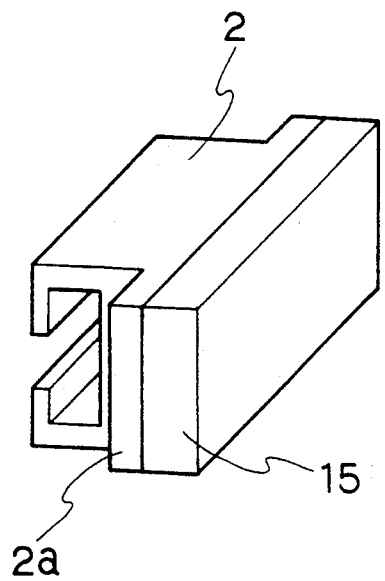
FIG. 8 is a perspective view illustrating another embodiment of the bracket used in the present invention.
Figure 9:
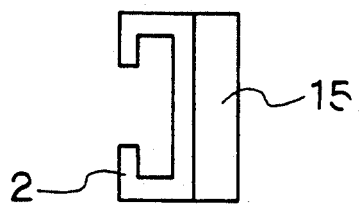
FIG. 9 is a sectional view illustrating yet another embodiment of the present invention.
Figure 10:
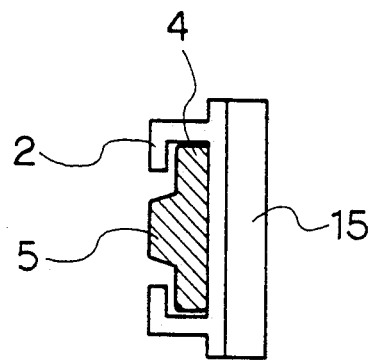
FIG. 10 is a sectional view illustrating a combination of the bracket and the wire of the present invention.
Figure 11:
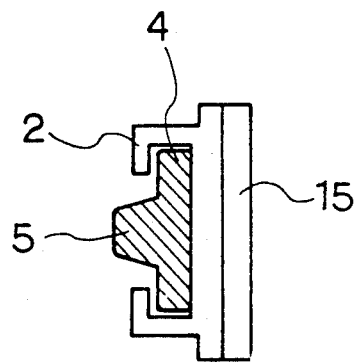
FIG. 11 is a sectional view illustrating another combination of the bracket and the wire.

With respect to the wire shown in FIG. 6, the wire is provided with two elongated projections 5 on the one side of the surface of the wire and the elongated groove 6 on the other side of the surface of the wire. The wire may be provided with the groove between two projections.

Hereinafter, the function and manner of use of the above-mentioned correcting device is described.

Figure 20:
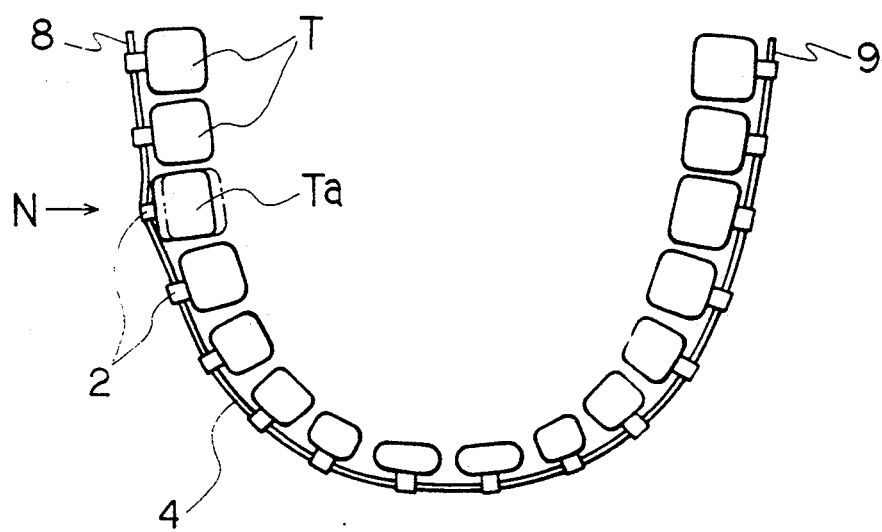
FIG. 20 is a plan view partly in section, showing a main part of another embodiment of the correcting device of the present invention.
Figure 21:
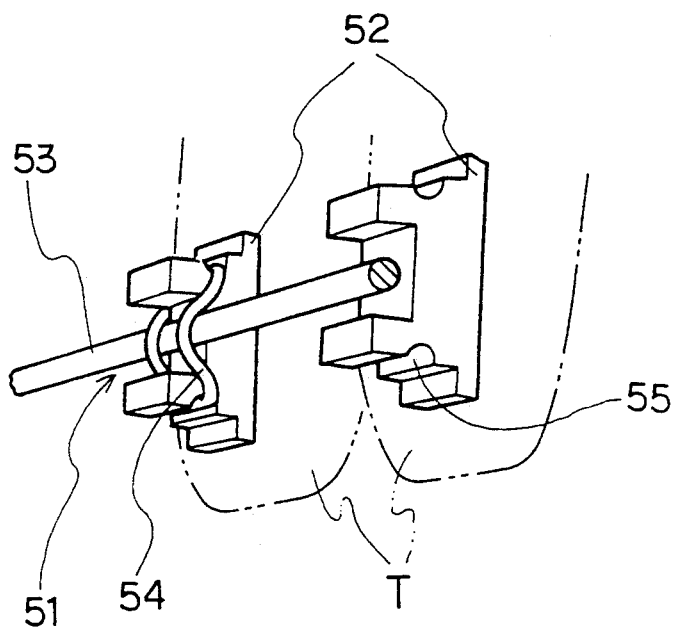
FIG. 21 is a perspective view illustrating an example of the conventional device for correcting teeth irregularities.

Firstly, bracket 2 is adhered to each tooth T as shown in FIG. 20. In such case, in accordance with the judgement of a dentist, the postures of brackets 2 are adjusted and lined in such manner that the spring force of the wire becomes useful for correcting the alignment of teeth, and fixed there by means of resin adhesive.

Next, the wire 4 is inserted through the series of slits 3 of the brackets 2 in order as shown in FIG. 1. At the time, the wire 4 can be set by inserting the end portion thereof from a T-shaped side openings of the slit 3 which is adhered to the back tooth which is in the deepest such as a molar. However, since the clearance between adjacent brackets 2 is narrow, it is convenient to insert the wire, and then to push the wire 4 in the slits 3 from the front openings thereof such that the wire is folded (FIG. 19) in the longitudinal direction by means of fingers F or a pair of tweezers.

The wire 4 pushed in the brackets 2 returns to the original flat shape soon due to elasticity thereof. And both side edges are caught with the nails 2b.

The wire 4 might be previously bent a U-shape as shown in FIG. 20, and might be partially bent in smaller radius of curvature or is partially deformed, inclined, twisted or the like at regions corresponding to the teeth to be moved.

Only by inserting the wire 4 through all brackets 2 as shown in FIG. 20, is attaching of the correcting device is finished. That is to say, it is not necessary to fasten the wire 4 to the brackets 2 with strings or the like, since the wire 4 is securely caught by the nails 2b. In addition, it is not necessary to fix the ends of the wire 4 with special brackets having a cylindrical shape which is necessary in conventional manner so that the wire 4 cannot slip along slits, in the brackets 2.

If the occasion arises, the ends of wire 4 might be folded and set with heat.

After installation of the wire 4, spring reaction force of the wire 4 is transmitted to the teeth Ta to be moved through the brackets 2. Consequently, the force (for example, about 20 to 200 g) shown in FIG. 20 by an arrow N is applied to the teeth Ta for a long time. As a result, the teeth Ta are moved in the direction of the arrow N gradually.

And besides, when a correcting torque in the twisting direction is required, a suitable correcting torque can be applied by merely changing the direction of the bracket 2, to be fixed on the tooth Ta, or by merely changing the shape of curvature of the wire 4. As the tooth Ta moves and then the wire 4 returns back to the original shape thereof, the spring force, i.e. correcting force, becomes weaker. In such condition, only the wire is changed for a new one with high stiffness, leaving the brackets 2 as they are. The old wire can be easily removed by catching the end and drawing out of the slits. If required, the wire can be previously cut into some pieces.

The new wire can be attached to the brackets 2 not only in such manner as shown in FIG. 19, but also by drawing out the old one after connecting with the old one.

The wire is generally changed about once per several weeks as occasion demands. That is to say, during the whole treatment period, a half to two years, the wire is changed several times.

Figure 12:
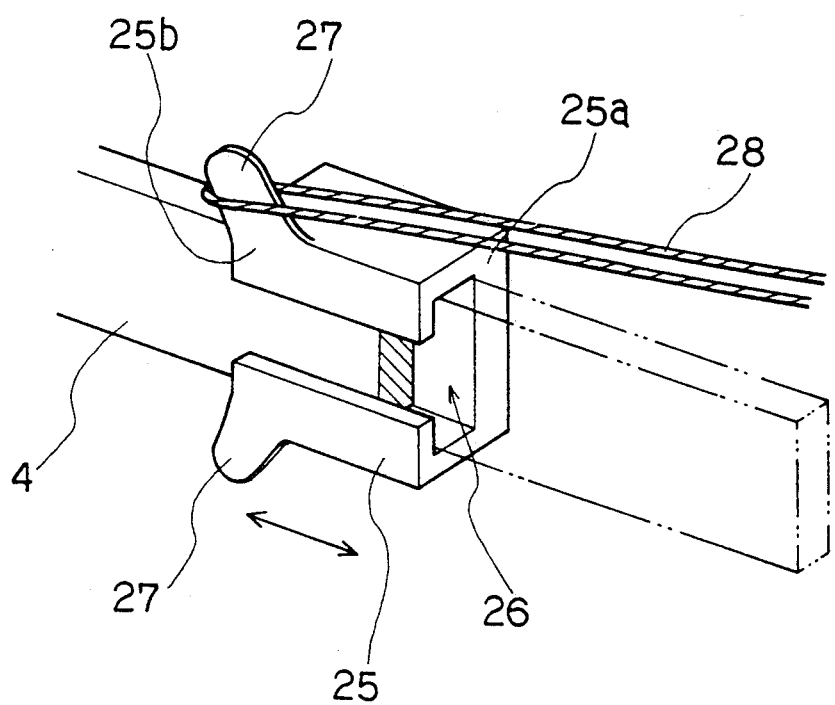
FIG. 12 is a perspective view partly in section, showing a main part of the supplementary device of the present invention.

In the above-mentioned embodiments, the brackets 2 are directly fixed on teeth as shown in FIG. 12.

However, it is more preferable that the bracket 2 is adhered to each tooth T through a base plate 15.

In this case, as a material of the base plate 15, it is advantageous for the device to employ material which is easily prepared. The base plate can be made from hard resin. The base plate is advantageously made from easily plastically deformable resin. The easily plastially deformable resin is a resin having a plasticity which is soft in beginning or which becomes plastic by applying heat. A thickness of the base plate ranges approximately from 0.5 to 5 mm in consideration of workability.

Next, a function of the base plate, which is made from easily plastically deformable resin, or the present invention will be explained in accordance with FIG. 7. FIGS. 7(a) to 7(d) are schematic plan views illustrating working steps wherein molding is performed to the tooth Ta to be corrected by using the base plate 15 and the base plate 15 is fixed to the tooth. The base plate 15 mounted on the base part 2a of the bracket 2 is abutted to the tooth (FIGS. 7(a) to 7(b)) to which the bracket 2 is fixed so that the base plate 15 is firmly molded. Since the base plate 15 has easily plastic deformability, the base plate 15 can be easily deformed and closely contacted with the surface of the tooth. In order that the base plate 15 is easily deformed, heat may be applied, if desired. When the material of the base plate does not have an adhesion property relative to the tooth, the molding work can be directly on the tooth of a patient without any pain. When the material of the base plate has the adhesion property relative to the tooth, or the tooth to be corrected is located in the place where molding work is hard to be performed, teeth irregularities are molded by using a gypsum beforehand.

The molded base plate 5 together with the bracket 2 are removed from the tooth (FIG. 7(C)), then cured. With respect to the resin having curing property, as means for curing, the means which has been conventionally used in the field of prosthodontia can be employed using heat, light, and the like. With respect to thermoplastic resin, the resin is cured by cooling.

As shown in FIG. 7(d), the bracket 2 having the cured base plate 15 is fixed to the corresponding tooth Ta by means of an adhesive (not shown). In the conventional technique wherein the bracket is fixed to the tooth by means of the adhesion, it is very difficult to adjust a quantity of the adhesive and a gap between the tooth and the bracket. On the contrary, according to the present invention the bracket can be easily fixed to the tooth with a slight adjustment. The wire is inserted into the slit of each bracket 2 which is respectively fixed to the tooth so that the plate of correcting teeth irregularities is created (FIG. 7(d)). The base plate which is made from easily plastically deformable resin can be applied to not only the conventional bracket but also the bracket which uses the wire having a rectangular shape in section.

The base plate is composed of the easily plastically deformable resin. As the easily plastically deformable resin, dental materials e.g. thermosetting resin such as epoxy resin, acrylic resin, phenolic resin, photocurable resin such as epoxy resin, acrylic ultraviolet crosslinking resin, thermosetting resin such as polyolefin resin, polyester resin, polyamide resin, polyimide resin, polycarbonate resin, which are conventionally known, can be employed.

As the adhesives, the adhesives which is conventionally known may be selected in accordance with the materials of the base plate. According to the present invention, the base plate has a surface wherein its shape can be closely contacted with the tooth so that the quantity of the adhesive is not great, a processing or a modification after bonding is remarkably reduced.

Next, a supplementary device for correcting teeth irregularities of the present invention will be concretely explained in accordance with FIG. 12. The supplementary device is useful for a sliding operation of the tooth when the supplementary device is used together with the above-mentioned correcting device (e.g. FIG. 14 or FIG. 15).

As shown in FIG. 12, the supplementary device 25 is provided with a wire-engaging-slit 26 having substantially the same shape as the slit 3 in the bracket so that the wire 4 is engaged with the slit 26. The engaging state of the supplementary device is the same as that of the bracket and the supplementary device is allowed to slide only in the direction along with the wire thereon. The slit 26 of the supplementary device 25 involves a nail part 25b and a base part 25a so that the slit is formed into a "T" shape. As shown in FIG. 12, the nail part 25b is provided with a protrusion 27 having a projecting edge which is vertically extending. As shown in FIG. 12, the nail part 25b may be provided with two protrusions 27 in both the upper and the lower marginal edges. The nail part 25b may have only one protrusion either in the upper or the lower marginal edge. In any case, a force applied to the tooth can be adjusted by selecting a location or combination of the protrusion 27 (e.g. FIG. 14). An elastic material such as rubber band 28 is engaged with the protrusion 27 so that a shrinkage force originates between two supplementary devices (referring to FIG. 14) each of which is stopped by the correcting device so as to be corded up.

Figure 13:
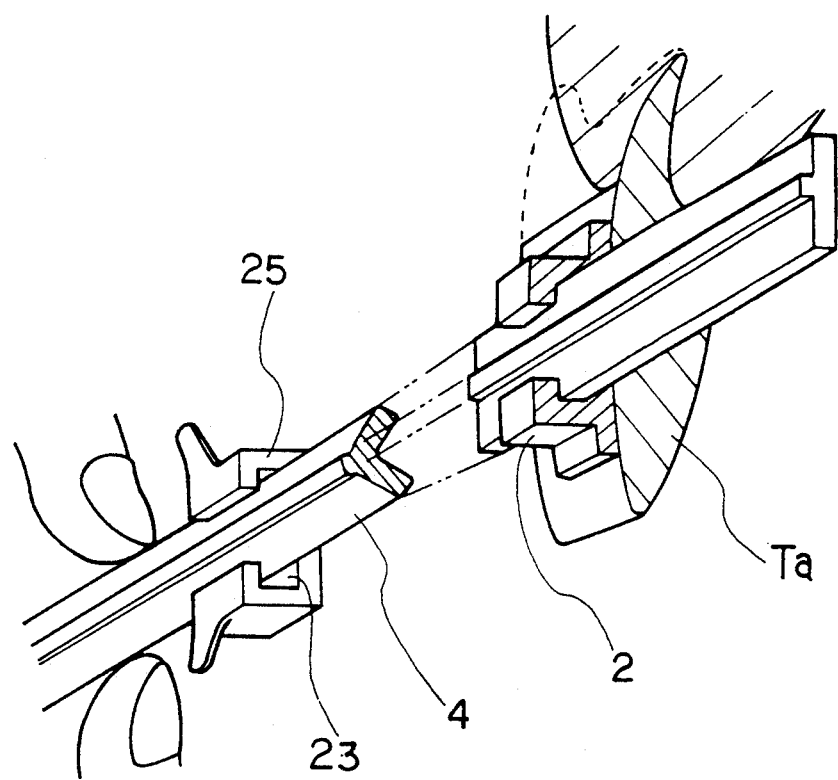
FIG. 13 is a perspective view partly in section, showing main part of an example showing a method for installating the supplementary device of the present invention.
Figure 14:
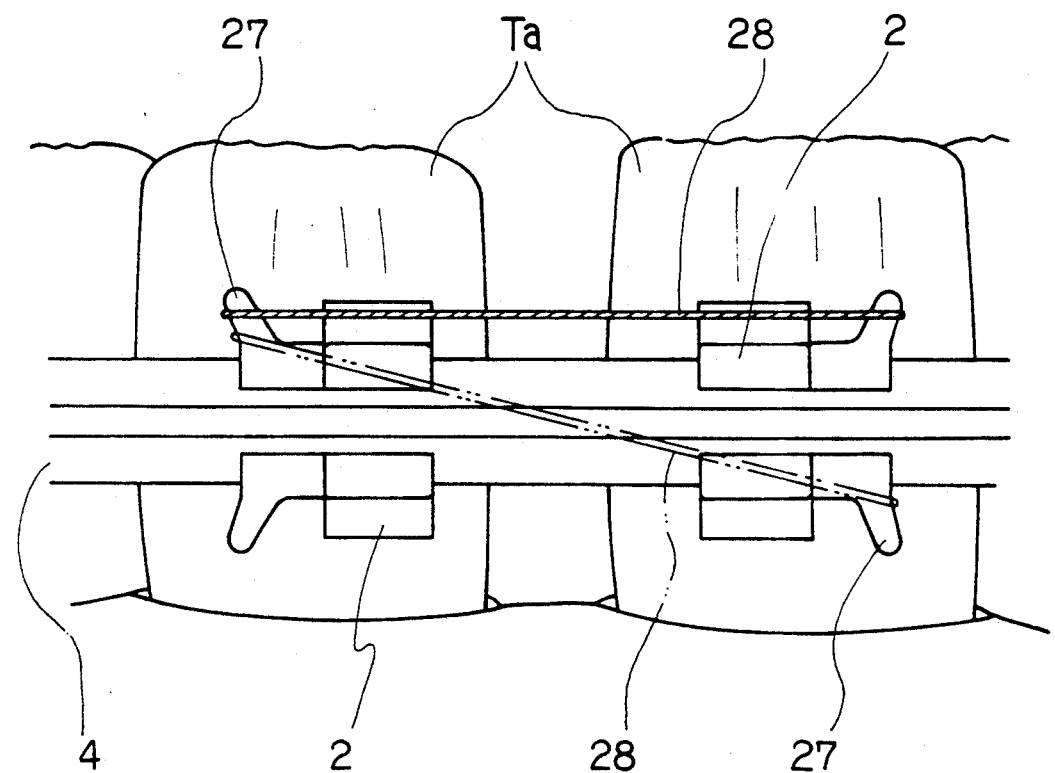
FIG. 14 is a front view illustrating an installed state of the supplementary device of the present invention.
Figure 15:
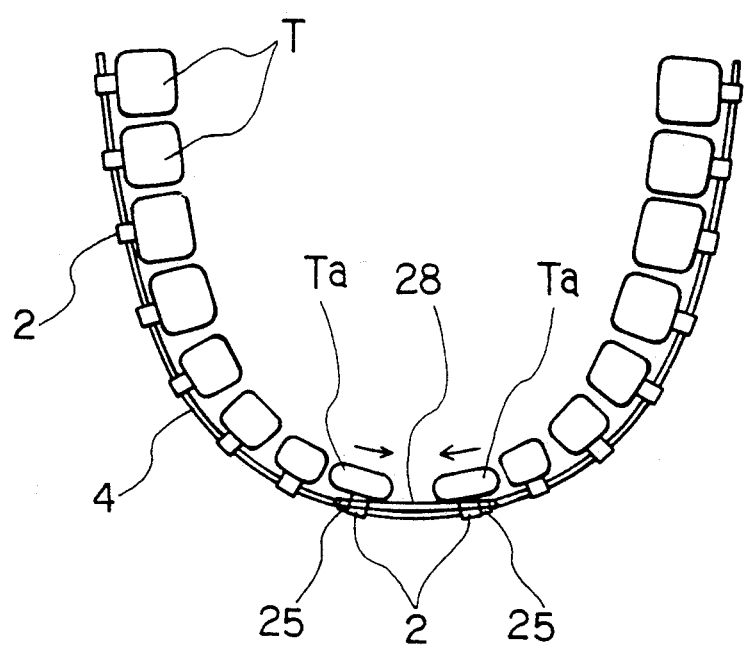
FIG. 15 is a plan view illustrating an example of the installed state of the correcting device using a supplementary device of the present invention.

Since the supplementary device 25 is slidable on the wire, the bracket plays the part of a stopper (FIGS. 13 and 14).

One feature of the present invention lies in that after the correcting device is once assembled and mounted on the tooth, the supplementary device is easily combined with the correcting device. That is to say, the wire 4 is pinched by a finger and a thumb so as to be bended (or folded) in the widthwise direction, and the wire 4 is engaged with the slit 23 of the supplementary device 25 so that the supplementary device 25 can be easily installed in the wire 4. Accordingly, when the twisted wire is returned to the normal posture and subjected to a sliding operation, installation and removal can be easily performed. In FIG. 14, a state of the supplementary device, which is installed by the rubber band 28 and combined with the bracket 2 and the wire 4, is illustrated. The rubber band 28 may be engaged with the protrusions 27 in parallel with the wire. The rubber band may be engaged with the protrusion diagonally. A schematic plan view of the supplementary device and the bracket, which are installed on the teeth, the illustrated in FIG. 15.

The supplementary device of the present invention can have several kind of features other than the device shown in FIG. 12.

Figure 16:
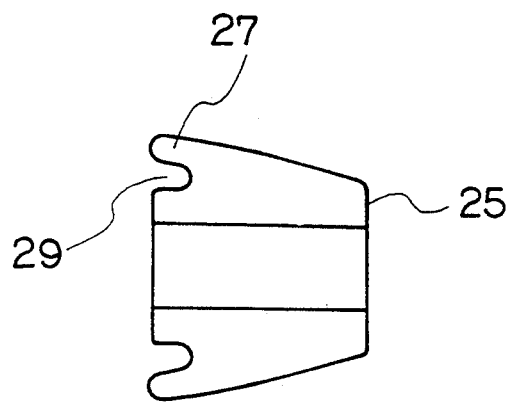
FIG. 16 is a plan view illustrating another embodiment of the supplementary device of the present invention.
Figure 17:
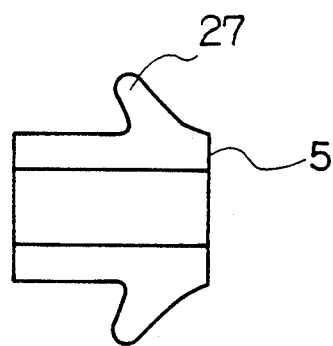
FIG. 17 is a plan view illustrating yet another embodiment of the supplementary device of the present invention.

For instance, as shown in FIG. 16, the supplementary device may have a shape, wherein the protrusion 27 is combined with a recessed portion 29, so that the rubber band is surely engaged with the protrusion. As shown in FIG. 17, the protrusion 27 may be formed on the nail part 25b near a location wherein the bracket is to be contacted.

Figure 18:
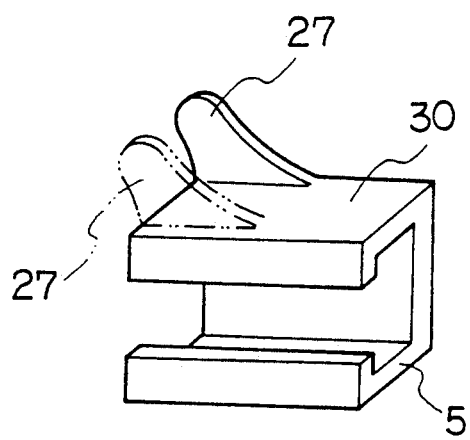
FIG. 18 is a perspective view illustrating yet another embodiment of the supplementary device of the present invention.

As shown in FIG. 18, the protrusion 27 may be shifted in the widthwise direction. The force applied to the tooth can be adjusted by changing the location of the protrusion. According to FIGS. 13 and 14, the supplementary device is installed in the wire so that the base part is opposed to the tooth (the base part is on the reverse side).

The supplementary device can be installed in the wire so as to be turned over. The protrusion is normally formed in side face 30 (FIG. 18) of the supplementary device so as to be in the direction extending across the wire in consideration of a strength and an easiness of producing the supplementary device. Any protrusion, wherein the rubber band can be engaged, may be employed. The supplementary device has preferably a dimension as follows. A width is in the range from 2 to 6 mm, a length is in the range from 1 to 5 mm and a thickness is in the range from 1 to 2 mm.

As the wire applied to the supplementary device, the wire having rectangular shape in section as well as the wire having an elongated projection or a groove can be employed.

The supplementary device can be used so as not to be fixed to the tooth. However, the wire is not excluded from being used so as to be fixed to the tooth. When the correction of the tooth is limited to the sliding operation, the bracket can be provided with the protrusion. The same effect is achieved from the correction of the tooth point of view. In the view point of a diversity of using and a treatment, the supplementary device is more advantageous.

The supplementary device can be made from the same materials as the bracket. Since the supplementary device is used for a relatively short period and is seldom fixed to the tooth compared with the bracket, the strength is not necessarily high. The base part can be relatively thin, then the supplementary device can be installed in the wire by bending the base part and opening the slit.

As mentioned above, the correcting device of the present invention has an advantage that setting of the device and changing of a wire is very easy due to the shape of bracket and cross section of the wire.

Therefore, a synthetic resin with rather less in anti-creepage property can be used as a material of the wire, since such disadvantage can be compensated by adding frequency of change of wires.

Therefore, since various synthetic resins having clear or white color can be freely used as a material of the wire, the present invention can satisfy a demand to use an incouspicuous wire.

According to the present invention, the bracket is firmly fixed to the tooth and a workability of installing the bracket on the tooth is improved.

Though several embodiments of the invention are described above, it is to be understood that the present invention is not limied to the above-mentioned embodiments, and various changes and modifications may be made in the invention without departing from the spirit and scope thereof.

What we claim is:

1. A device for correcting teeth irregularities comprising:
   a bracket to be fixed on tooth, said bracket having a slit with T-shaped section; and
   a wire to be inserted into said slit and thereby be engaged with said bracket; said wire being provided with an elongated projection and having a "T" like shape in section.

2. The device of claim 1, wherein said wire is composed of plastic material.

3. The device of claim 2, wherein said wire includes a reinforcement member for said plastic material.

4. The device of claim 2, wherein said plastic material has a non-oriented crystallization.

5. The device of claim 1, wherein said wire has a surface, said surface having a groove extending along a longitudinal direction of said surface thereof.

* * * * *